(12) United States Patent
King

(10) Patent No.: US 7,146,224 B2
(45) Date of Patent: Dec. 5, 2006

(54) APPARATUS FOR MULTIPLE SITE STIMULATION

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 199 days.

(21) Appl. No.: 11/039,214

(22) Filed: Jan. 19, 2005

(65) Prior Publication Data

US 2006/0161236 A1   Jul. 20, 2006

(51) Int. Cl.
*A61N 1/05* (2006.01)
(52) U.S. Cl. ..................................... 607/117
(58) Field of Classification Search ............... 607/46, 607/115–117, 122, 129; 600/393, 377, 374, 600/373, 378
See application file for complete search history.

(56) References Cited

U.S. PATENT DOCUMENTS

| | | | |
|---|---|---|---|
| 5,501,703 A | 3/1996 | Holsheimer et al. | |
| 5,643,330 A | 7/1997 | Holsheimer et al. | |
| 5,895,416 A | 4/1999 | Barreras, Sr. et al. | |
| 6,038,480 A | 3/2000 | Hrdlicka et al. | |
| 6,236,892 B1 | 5/2001 | Feler et al. | |
| 2003/0055476 A1 | 3/2003 | Vinup et al. | |
| 2005/0038489 A1 | 2/2005 | Grill | |

OTHER PUBLICATIONS

Holsheimer J., and Wesslink WA, "Effect of Anode-Chaode Configuration on Parestheisa Coverage in Spinal Cord Stimulation", Neurosurgery, Sep. 1997, pp. 654-659, Vo. 41(3).
Holsheimer J., et al., "Clinical Evaluation of Paresthesia Steering witha New System for Spinal Cord Stimulation", Neurosurgery, 1998, No. 3, pp. 541-547, vol. 42.
Claeys L., "Spinal Cord Stimulation and Chronic Critical Limb Ischemia", Neuromodulation, 1999, vol. 2, No. 1.
Slavin KV et al., "Efficacy of Transverse Tripolar Stimulation for Relief of Chronic Low Back Pain", Stereotactic & Functional Neurosurgery, 1999, pp. 126-130, vol. 73.

*Primary Examiner*—Robert E Pezzuto
(74) *Attorney, Agent, or Firm*—John W. Albrecht

(57) ABSTRACT

An implantable medical device for stimulating electrically excitable tissue within a patient, and more particularly relates to such a system having a pulse generator and a lead. The lead includes a first set of electrodes including at least three electrodes. The lead also includes a second set of electrodes including at least first, second and third electrodes. The first and second electrodes are positioned on opposite sides of an imaginary longitudinal axis that passes through the center of the third electrode. The second set of electrodes is located at or nearer to the proximal portion of the lead relative to the location of the first set of electrodes.

20 Claims, 17 Drawing Sheets

APPARATUS FOR MULTIPLE SITE STIMULATION

FIELD OF THE INVENTION

The invention relates to an implantable medical device including at least two electrode sets for electrically stimulating at least two sites of the nervous system.

BACKGROUND

Spinal cord stimulation (SCS) using electrical pulses of constant or varying frequency, amplitude and pulse width has been done for many years to treat chronic neuropathic pain of the trunk and limbs. Usually after a percutaneous trial has shown efficacy, a complete medical device is implanted surgically, so that long-term therapy can be done, often for many years. The typical device has a pulse generator in a subcutaneous position that generates the electrical pulses, a multiwire extension to bring those pulses near to the spinal column, and a delicate lead or two with multiple electrodes to deliver the pulses within the spinal canal.

Early attempts placed the multielectrode leads next to the spinal cord so that neurons less than a millimeter away could be activated. This required significant and invasive surgery to open the dura covering the spinal cord, or to develop a space between the dura and the arachnoid membrane. It the lead moved or developed open circuits, efficacy was lost, or morbidity such as infection developed, the lead had to be removed or replaced with additional neurosurgical procedures. Such early leads were also delicate, to not compress the spinal cord.

Today, the preferred lead location is outside the dura, in the epidural space. This location has benefits such as quicker and easier surgical access to implant, minimization of unwanted side effects such as possible leakage of cerebrospinal fluid, and less difficulty to remove or replace the lead, should infection, loss of effectiveness, or lead migration or breakage occur. In this case, the electrodes are usually two to six millimeters away from the targeted neurons. Between them and the neurons to be excited are the dura, arachnoid membrane and a layer of highly conductive cerebrospinal fluid. These elements tend to diffuse the electrical currents, and boost the amplitudes needed for activation as much as ten-fold.

To better select the neurons that might be excited, multielectrode leads have been developed. The complete system allows programming, so that each pulse sent from the pulse generator can be delivered to the tissue through one or more cathodes and the current returns to the pulse generator through one or more anodes. Usually the neurons near the cathodes are depolarized sufficiently to create action potentials, especially at narrow pulse widths of 500 microseconds or less, when approximately square-wave pulses are used. It has been learned clinically and with the use of electrical models of the spinal cord (see Holsheimer J and Wesselink W A, *Neurosurgery*, vol. 41, pp 654–659, 1997) that the orientation of the anodes and cathodes with respect to the neurons is relevant. Activation usually requires that there be a component of the electric fields produced (actually, the second spatial derivative) that is parallel to the neuron's axon, and this can lead to electrical currents of sufficient intensity to initiate action potentials along axons.

There is a need to effectively stimulate two different vertebral levels to treat pain in different anatomical locations. It is also desirable to have the capability to steer the fields at these locations. Field steering may be provided by tripole stimulation. Tripole stimulation occurs when there is a set of three or more electrodes and at least two of the electrodes are pulsed overlapping in time. Tripole stimulation may be either transverse tripole stimulation (TTS) or longitudinal tripole stimulation (LTS). TTS is defined in this application as occuring when the first and second electrodes are positioned on opposite sides of an imaginary longitudinal axis that passes through the center of the third electrode and parallel to the longitudinal axis of the lead. LTS occurs when the electrodes are substantially oriented along the longitudinal axis of the lead.

Peer-reviewed publications of results from studies using devices delivering transverse tripole stimulation (TTS) have shown that TTS is quite effective in delivering paresthesia and relief of pain in the legs and feet when done at T10 to L1 vertebral levels (see Holsheimer J et al., *Neurosurgery*, Vol. 42, No. 3, pp 541–547, 1998; Wesselink W A et al., *Neuromodulation*, Vol. 2, No. 1, pp 5–14, 1999). However, when TTS was done at higher levels of T8–T9, specifically to treat low back pain, and even as low as L1, it was not shown to significantly relieve low back pain (see Slavin K V et al., *Stereotactic & Functional Neurosurgery*, Vol. 73, pp. 126–130, 1999).

Because TTS provides better results at certain anatomical regions and LTS to other anatomical regions it is desirable to have a lead having the capabilities to deliver TTS and LTS to the desired locations. Many of the anatomical regions for which TTS works well are at a lower vertebral level than the regions for which LTS works well. It is also generally preferred to perform orthograde insertion of leads (that is insertion in the direction from lower vertebral levels to higher vertebral levels). There is therefore a need to provide a method and lead that provides both TTS and LTS wherein the TTS electrodes are at a lower vertebral level than the LTS electrodes.

SUMMARY

One embodiment of the invention is an implantable medical device for stimulating electrically excitable tissue. The medical device includes a pulse generator and an implantable lead. The lead includes a first set of electrodes including at least three electrodes configured for electrical communication with the pulse generator. The lead also includes a second set of electrodes including at least first, second and third electrodes configured for electrical communication with the pulse generator. The first and second electrodes are positioned on opposite sides of an imaginary longitudinal axis that passes through the center of the third electrode. The second set of electrodes is located at or nearer to the proximal portion of the lead relative to the location of the first set of electrodes. The distance between the distal most electrode of the second set of electrodes and the proximal most electrode of the first set of electrodes is at least three centimeters.

Another embodiment is an implantable lead having a proximal portion and a distal portion. The lead includes a first set of electrodes including at least three electrodes configured to receive pulses from a pulse generator. The lead also includes a second set of electrodes including at least first, second and third electrodes configured to receive pulses from the pulse generator. The first and second electrodes are positioned on opposite sides of an imaginary longitudinal axis that passes through the center of the third electrode. The second set of electrodes are located at or nearer to the proximal portion of the lead relative to the location of the first set of electrodes. The distance between the distal most electrode of the second set of electrodes and the proximal most electrode of the first set of electrodes is at least three centimeters.

BRIEF DESCRIPTION OF THE DRAWINGS

The accompanying drawings which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout.

DETAILED DESCRIPTION

Figure 1:
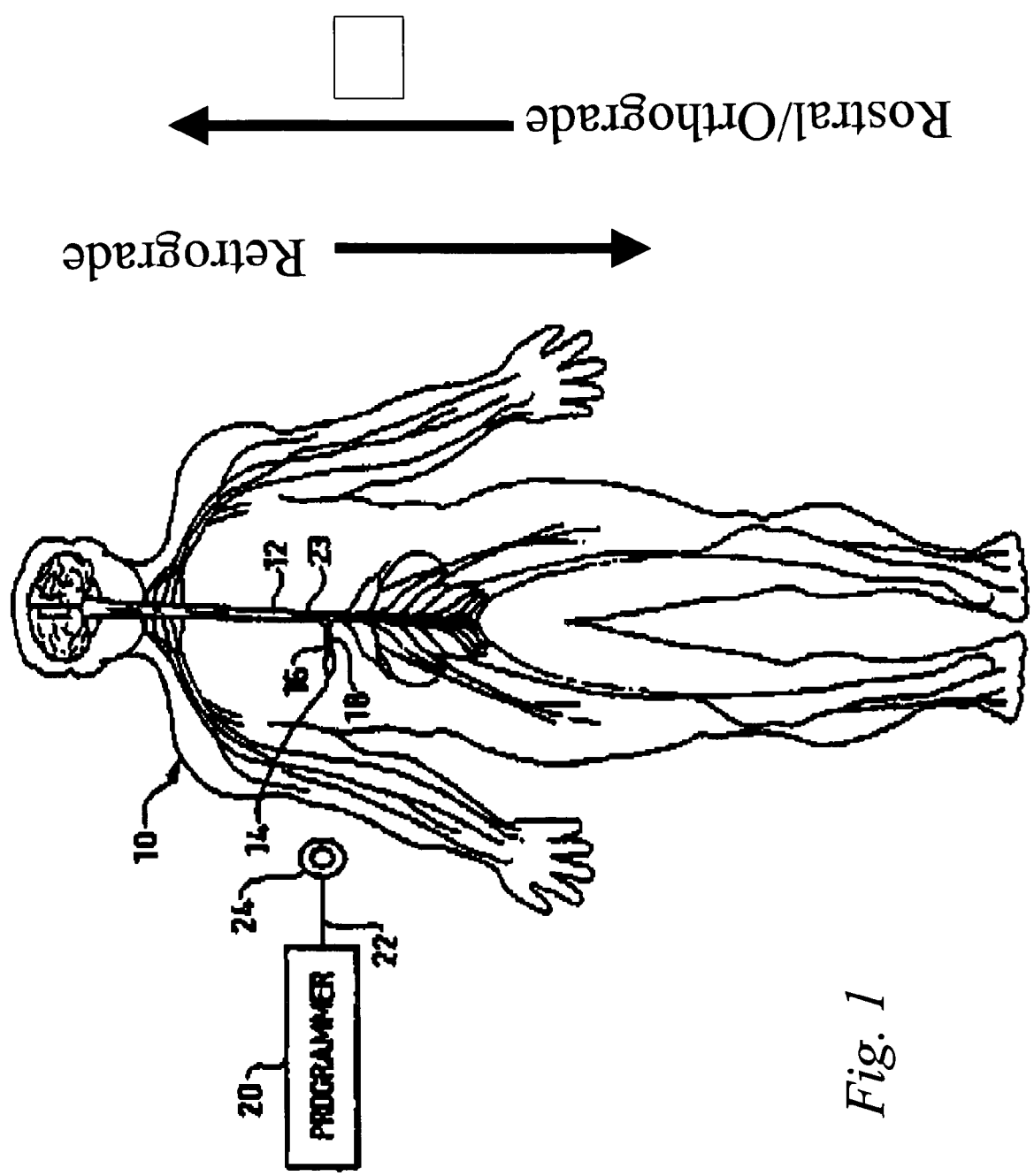
FIG. 1 is a frontal view of a patient with an implanted spinal cord stimulation system and an external control device.

FIG. 1 illustrates an implanted system to accomplish pain relief in a patient 10 who has chronic pain. While it will be described herein with reference to SCS procedures and the embodiments described in relation to electrical therapy, it will be recognized that the invention finds utility in applications other than SCS procedures, including other applications such as Sacral Root Stimulation, or Intraventricular Cerebral Stimulation. In addition, the invention finds applicability to SCS or CSS procedures where the lead is placed in the intrathecal (subdural) space.

FIG. 1 shows the implanted components of a medical device, consisting of a pulse generator 14 connected to an extension 18 and then to a multielectrode lead 23, that has a distal portion passing through the intervertebral space and positioned substantially parallel to the spinal cord 12. The implanted medical device provides treatment therapy to at least two anatomical sites. In one embodiment, the implanted medical device specifically delivers therapy to treat pain. The pulse generator may generate sequences of electrical pulses of constant amplitude, pulse width and frequency. These pulse parameters can be adjusted, and the polarities of active electrodes selected, either by stored programs in the pulse generator 14, or by radiofrequency telemetry from an external antenna 24 connected to an external programming device 20. This specification describes preferred lead characteristics and pulse generator outputs that can optimally provide treatment therapy in at least two areas of the body, using at least two sets of electrodes with carefully designed orientations with respect to the anatomy and physiology of the spinal cord.

Figure 2:
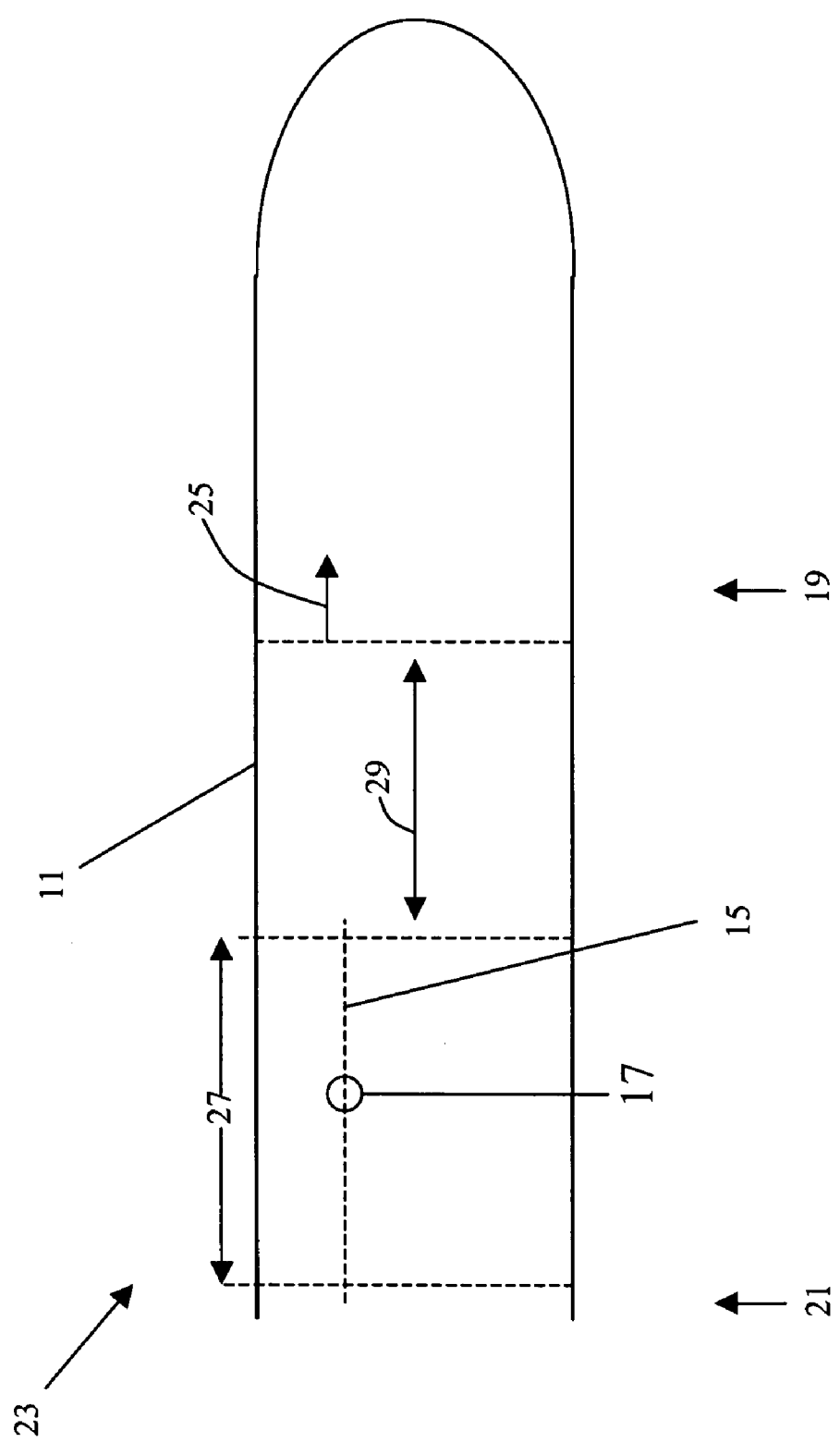
FIG. 2 is a ventral view of the side toward the spinal cord of the distal end of a concept of a lead (not all electrodes shown) that has first and second sets of electrodes.

FIG. 2 shows a conceptual illustration of a portion of an implantable lead 23 according to one embodiment of the invention. The implantable lead 23 has a distal portion 19 and a proximal portion 21. Note that the terms distal portion and proximal portion are used here in a relative manner to indicate that the distal portion is distal as compared to the proximal portion. The implantable lead 23 includes a lead body 11. A first set of electrodes (not shown) is coupled to the lead body 11 and resides in some area (designated as area 25 in FIG. 2) at or near the distal portion 19 of the lead. The implantable lead also includes a second set of electrodes coupled to the lead body 11 and residing in area 27 including at least first electrode (not shown), second electrode (not shown) and third electrode 17. The first and second electrodes are positioned on opposite sides of an imaginary longitudinal axis 15 that passes through the center of the third electrode 17. The term "imaginary longitudinal axis" indicates an axis coincident with or parallel to a line passing through the center of the lead body extending in the longest dimension of the lead body. The second set of electrodes is located at or nearer to the proximal portion of the lead relative to the location of the first set of electrodes 25, and wherein a first distance 29 (shortest distance from edge of one electrode to edge of the other electrode) between the distal most electrode of the second set of electrodes and the proximal most electrode of the first set of electrodes is at least three centimeters. In alternate embodiments the first distance 29 may be at least four centimeters, at least five centimeters, or at least six centimeters.

The electrodes of both sets of electrodes are configured to receive pulses from a pulse generator. The pulses may be delivered by any means. In one embodiment, the pulses are delivered to the electrodes by electrical conductors.

Field steering may be accomplished with tripole stimulation by providing two or more pulses overlapping in time to two or more electrodes in a tripole. For purposes of this application, the term "overlapping in time" means that at least a portion of each of the pulses being referred to exist at the same time. "Overlapping in time" does not require that the pulses being referred to start and end at the same time. Pulses that are referred to as simultaneous are included in (as a subset) the definition of "overlapping in time".

Figure 3:
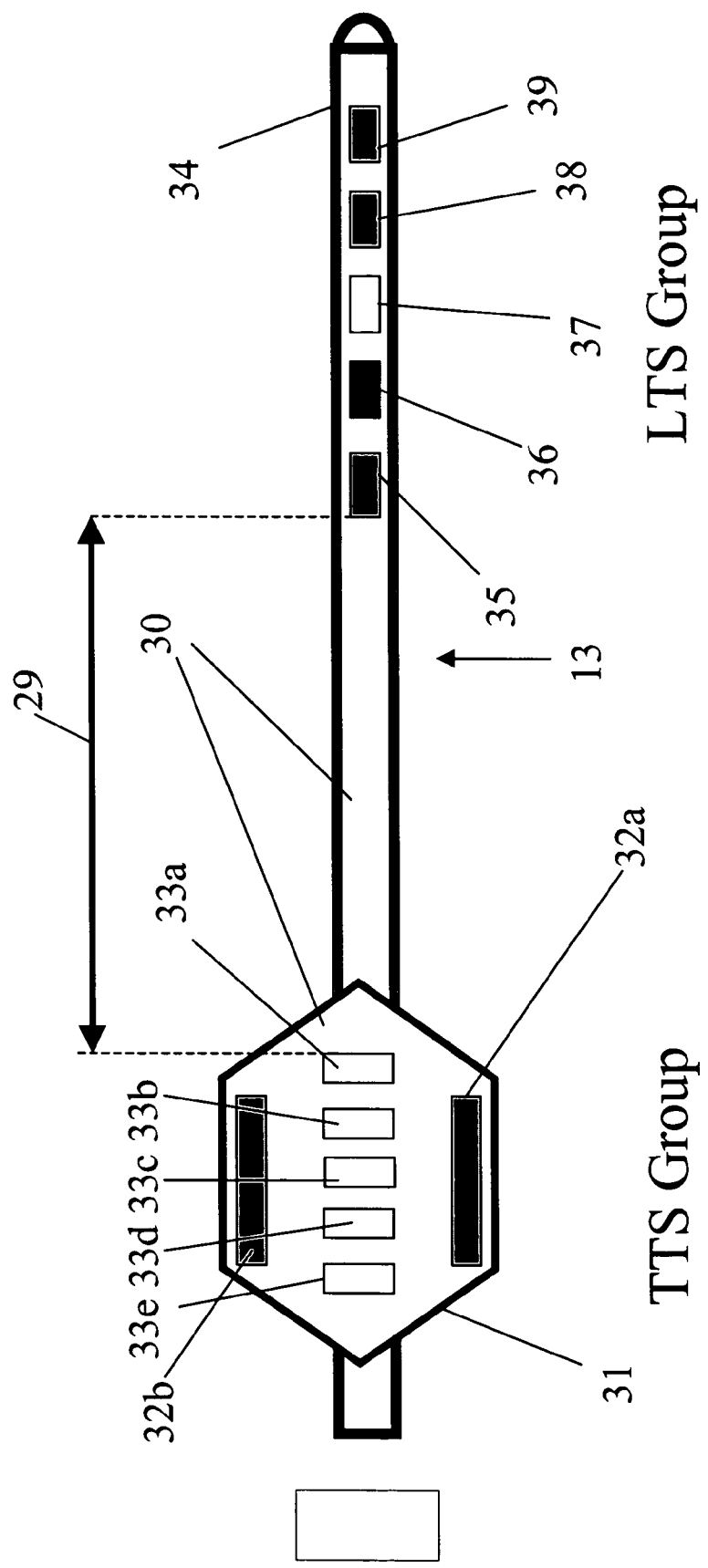
FIG. 3 is a ventral view of the side toward the spinal cord of the distal end of a lead that has both an LTS part and several TTS parts, separated by an appropriate distance to treat both back pain and leg or foot pain.

FIG. 3 shows a view of the ventral side (the side positioned toward the spinal cord) of the distal part of a spinal cord stimulation (SCS) lead 13 according to one embodiment of the lead 23. Lead 13 includes lead body 30. The lead body 30 extending caudally (truncated in the view) and the distal tip 34 more rostrally are cylindrical, with a diameter of approximately one to two millimeters, and consists of an elastomeric, nonconductive polymer, with at least one channel inside for a steering stylet and at least one channel for wires going to the electrodes. There are two sets of electrodes. The first set of electrodes includes electrodes 35-39 that are arranged for longitudinal tripole stimulation (LTS) such that field steering may be achieved by the application of two or more pulses overlapping in time with each other on two or more electrodes and the ability to independently control the amplitudes of the two pulses. This first set of electrodes is at the distal portion of the lead. Each electrode in the first set of electrodes in this embodiment is preferably two to six millimeters in longitudinal length, and separated from one another by one to five millimeters. In one embodiment, the electrodes of lead 13 are composed of relatively inert and low impedance metal, such as platinum/iridium. In one embodiment, this first set of electrodes is designed to treat low back pain, and the center of the set will be positioned preferably on the physiological midline in the vicinity of the T8 or T9 vertebral level. This vertebral level is relatively near to the entry of the L2 dorsal roots in the spinal cord, or slightly more rostral.

The second set of electrodes in FIG. 3 consists of a first electrode 32a and second electrode 32b on opposite sides of an imaginary longitudinal axis passing through third electrode. The third electrode in this embodiment may be any one of the electrodes 33a–e. In this embodiment there are five electrodes in the path of the imaginary longitudinal axis (the axis passing through the third electrode 33 and parallel to the axis of the lead body) for better control and steering of the electric field. This second set of electrodes can perform transverse tripole stimulation (TTS), which has benefits for treating certain locations such as to treat pain of the legs and feet. In this particular embodiment, the lateral electrodes 32a and 32b and any one of the electrodes 33a–e constitute an approximately collinear set of electrodes that are substantially perpendicular to the axis of the lead. The center of this set is positioned on the physiological midline at a spinal level that allows it to deliver precisely controlled paresthesia, and hence pain relief, in all parts of the body below the beltline, preferably at the T10–L2 vertebral level.

The lead body 30 of lead 13 includes a wider, paddle-type element 31 containing the second set of electrodes. This might be rigid enough to stay flat in the epidural space, or curved to match the shape of the dura, and approximately 10–14 mm in width. Its width may necessitate using a laminectomy-type surgical insertion. Or, it might be thinner and more pliable, and able to curl upon the lead body during insertion via a Tuohy needle or catheter, as described in U.S. Pat. Nos. 6,161,047; 6,292,702; and 6,442,435 by King G et al., hereby incorporated by reference in their entirety. The term "width" of the lead body as used in this application means the greatest width within a certain region. For example, if the width is not constant along a set of electrodes then reference to the width at the first set of electrodes means the maximum width in the area 25. Likewise width at the second set of electrodes means the maximum width of the lead body in the area 27.

Preferably both the first set of electrodes and the second set of electrodes are optimally positioned along the spinal column to accomplish their respective optimal pain relief therapies. Hence, the lead may be made in several lengths, with different longitudinal spacings of the two sets of electrodes. An implanting physician would study the patient history and sites of pain, and also make operating room observations such as trial SCS and motor effects at low frequency, and perform tests like using somatosensory evoked potentials to determine the best spacing between the sets, and then would position the lead in the epidural space, anchoring it in subcutaneous tissue to keep it in this optimal position. Since the TTS group (second set of electrodes 32a, 32b, and 33a–e) is preferentially going to recruit dorsal column axons, and they are oriented longitudinally in parallel fashion to the lead body, the rostral/caudal position of the TTS set of electrodes may not be as critical as the rostral/caudal position of the LTS set of electrodes (first set of electrodes 35–39), which might be mainly exciting dorsal root fibers.

Some embodiments of this invention utilize field steering by control of the amplitude of a stimulation pulse. It is importantly noted that the amplitude being controlled may be current amplitude or voltage amplitude of the stimulation pulse. It is also within the scope of this invention to utilize a system in which one or more channels are current controlled and one or more channels are voltage controlled.

Figure 4:
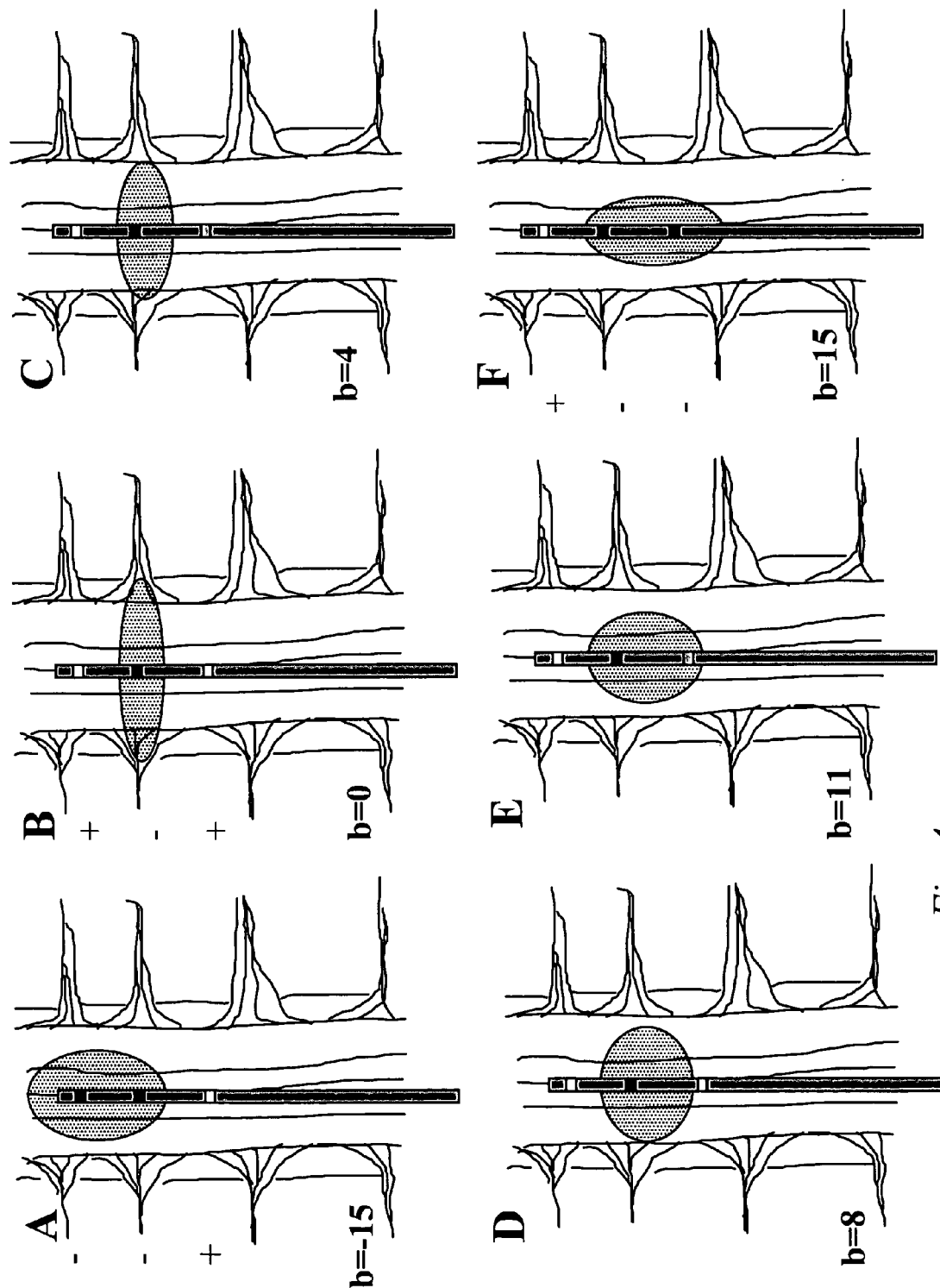
FIG. 4 is a schematic view of six typical neuronal recruitment areas that could be achieved using the LTS electrodes at the distal end of the lead in the prior FIG. 2.

FIG. 4 is a schematic view of six out of many useful neuronal recruitment areas that could be achieved using the LTS electrodes at the distal portion of the lead in the prior FIG. 3. The lead has three electrodes. The lead is to be positioned at the T8–T10 vertebral levels, and placed closed to the physiological midline, unless operating room observations indicate that a slightly more lateral position is more beneficial. In FIG. 4A, the three electrodes all have full polarity, i.e., the top two are cathodal (−), and each receives the same amplitude negative voltage pulse. The bottom electrode is an anode (+), and provides a return path for cathodal current leaving the top two electrodes. Many commercially available stimulation systems today could accomplish this, and having two or more cathodes connected in parallel to a cathodal pulse are commonly used on patients. The power source will provide at least two pulses overlapping in time of different amplitude, usually voltage controlled or current controlled. It can do this in analog fashion, with many possible fine changes in the two amplitudes. Or, it may do it in discrete steps, as described in the articles by Holsheimer J and Wesselink W A above, and in Table 1 below. In this figure, we shall describe 31 steps of relative amplitudes of the overlapping in time pulses to the electrodes. This shall be termed, "balance", or, "b". The steps can range in integer differences, from b=−15, to b=+15. In FIG. 4A, b=−15, so the cathodal amplitude in the top electrode is equal to the cathodal amplitude in the middle electrode. The shaded oval is a depiction that with this electrode configuration, activation of axons might be mostly those under the cathodes, and near the midline of the spinal cord, hence, axons in the dorsal columns.

In FIG. 4B, the balance has been set to b=0. In this case, again, full polarities are used, and both the top electrode and the bottom are full anodes (+), and the middle electrode is a cathode (−). There are 14 other steps available between these two situations, in which the pulse to the top electrode is progressively less negative (cathodal) and instead more positive (anodal). In this figure, the area of recruited axons is constrained to lie between the two anodes, and, as amplitude is increased, it will activate dorsal roots as it becomes wider.

In FIG. 4F, again, full anodes or cathodes are used. Balance b=+15, and the bottom two electrodes are cathodes (−) and the top one is an anode (+). Here again, the recruited zone is under the cathodes, and slightly oval with the longer diameter in a direction parallel to the spinal cord, only lower than in FIG. 4A.

In FIG. 4C, FIG. 4D and FIG. 4E, the balance has been adjusted to lie between b=0 and b=+15. As the balance step is increased, the zone of recruited axons changes its shape from a transverse oval (FIG. 4B) to a longitudinal oval (FIG. 4F). Hence, this invention allows a fine balance in the amount of axons recruited that are longitudinal (dorsal columns of the spinal cord) versus transverse (dorsal roots of spinal nerves). This gives a very fine control of whether the paresthesia produced is in just one dermatome (where one spinal nerve has its dorsal roots under the cathode) or many dermatomes (where dorsal column fibers from many dermatomes are recruited).

This invention may use discrete steps in the relative amplitudes, with some of 31 balance steps shown in FIG. 4, of cathodal pulses to some of the LTS set electrodes, or it may use analog signals, and thus very many or infinite control of the relative amplitudes. The LTS effect might be done with control of electric pulses passing to the cathodes or the anodes, and more than three collinear electrodes might be active.

Figure 5:
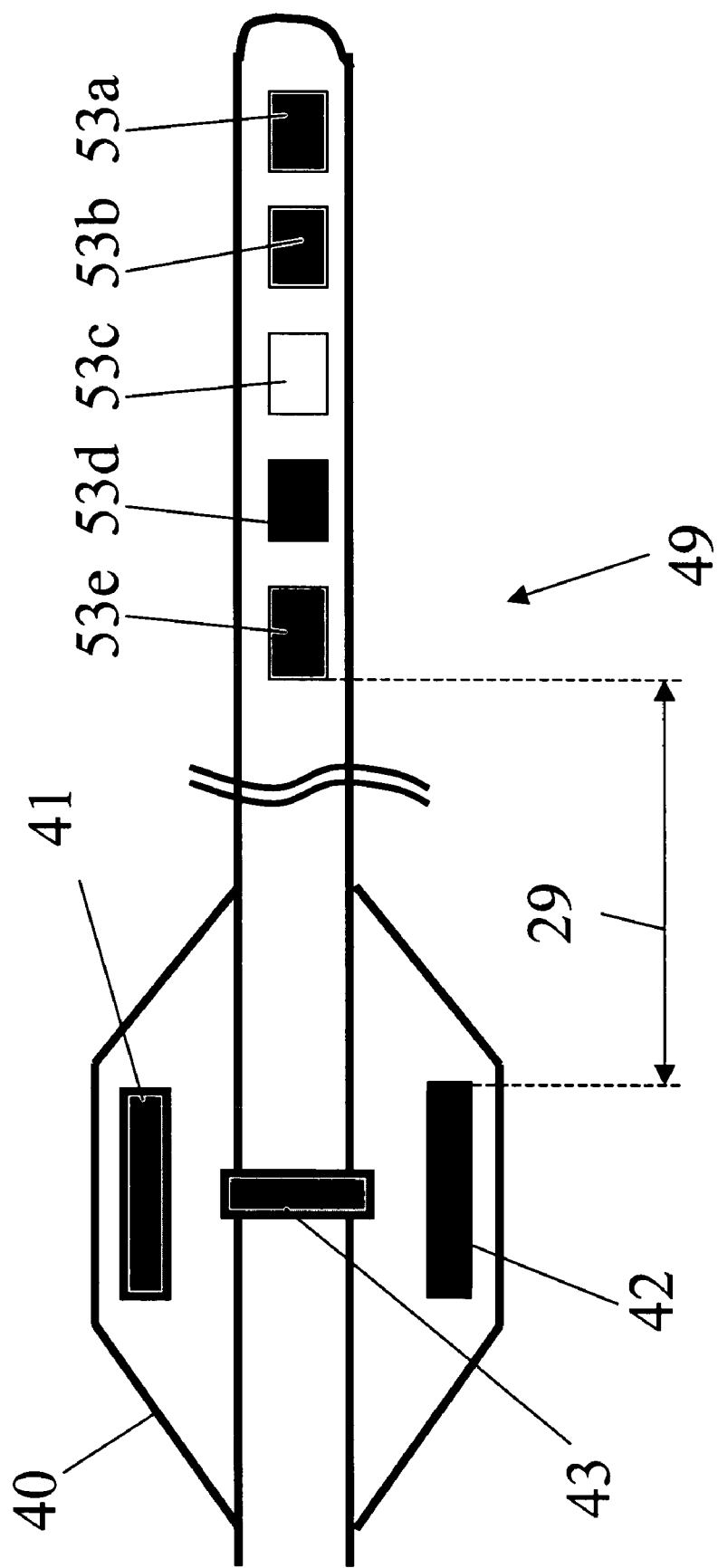
FIG. 5 is a ventral view of the distal end of a lead that has one LTS part and one TTS part, separated by an appropriate amount to treat both back pain and leg or foot pain.

FIG. 5 is a ventral view of the distal end of another embodiment of lead 23, namely lead 49. Lead 49 includes a first set of electrodes 53a–e capable of performing LTS and a second set of electrodes 41–43 capable of performing TTS, separated by a distance to treat both back pain and leg or foot pain. Here, only one central electrode 43 is located in the second set of electrodes.

Figure 6:
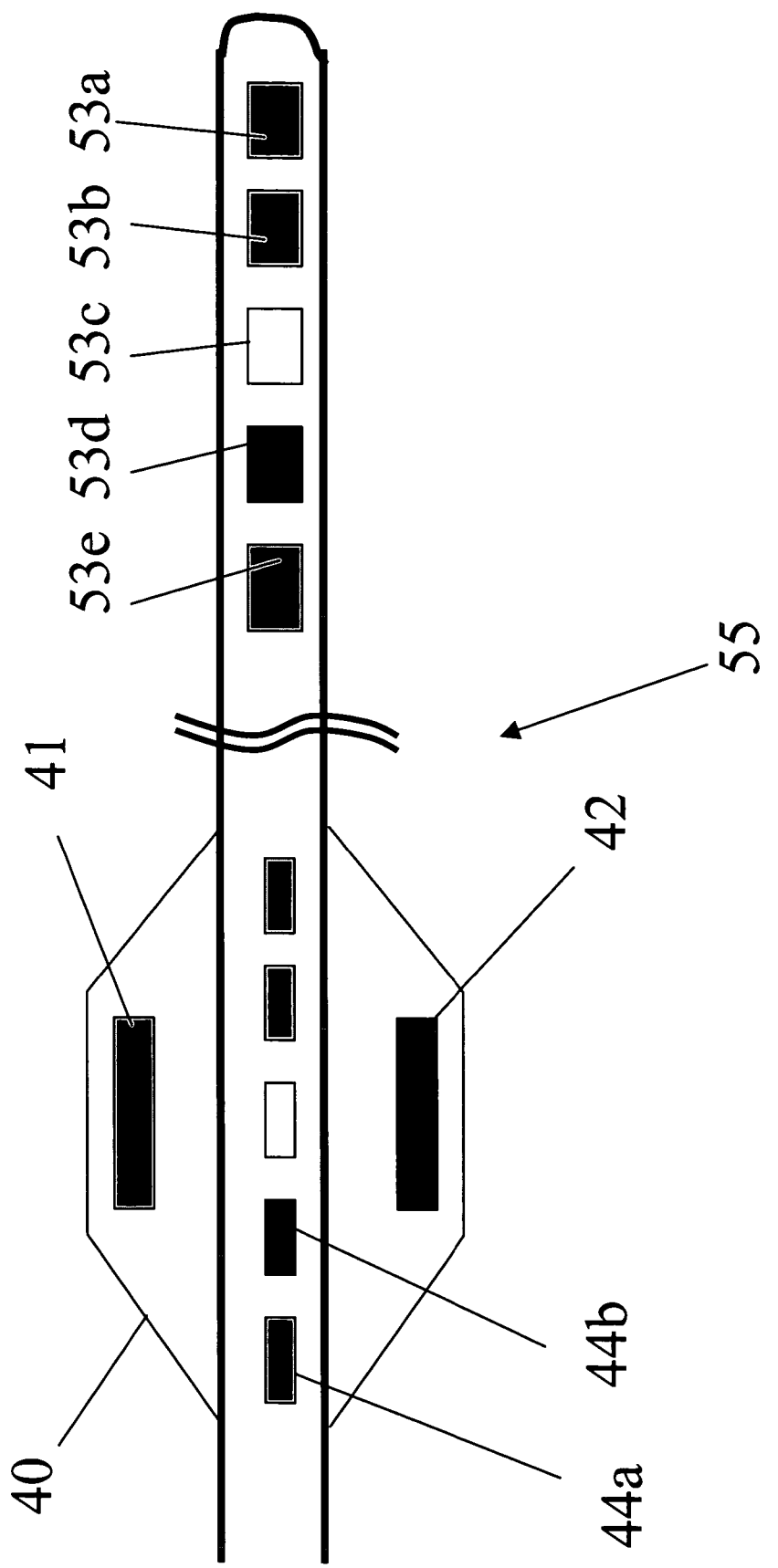
FIG. 6 is a ventral view of a lead with both an LTS part and a TTS part, with the central electrodes of the TTS part having a less wide dimension to make positioning of the lead less sensitive to physiological midline.

FIG. 6 is a ventral view of a lead 55 that is one embodiment of lead 23. Lead 55 includes a first set of electrodes 54a–e capable of performing LTS and a second set of electrodes 41, 42, and 44a–e capable of performing TTS, with the central electrodes 44a–e of the second set of electrodes having a less medial/lateral dimension than a longitudinal (rostral/caudal) dimension. This is designed to make positioning of the lead less sensitive to its placement on the physiological midline. This design helps to prevent unacceptable activation of the dorsal roots when the lead moves laterally after implantation, or subsequent scar tissue diverts the currents from the electrodes.

Figure 7:
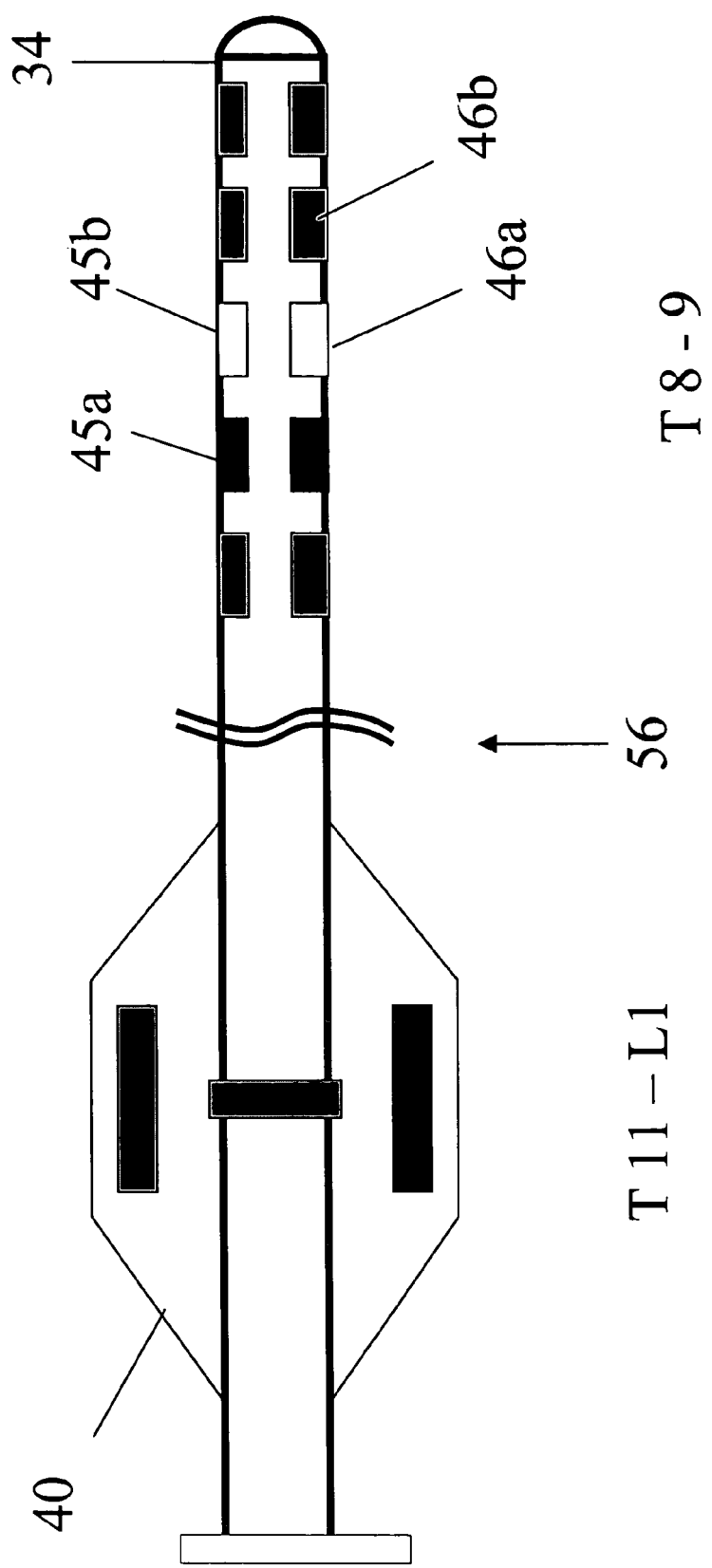
FIG. 7 is a ventral view of a lead with two LTS columns of electrodes and one TTS part to give more options in treating the back pain.

FIG. 7 is a ventral view of another embodiment of lead 23, namely lead 56. Lead 56 includes a first set of electrodes that includes two columns of electrodes to give more options in treating back pain. A second set of electrodes is also provided that is capable of TTS. Electrodes 45a and 45b would be more to the right side of the patient, and electrodes 46a and 46b toward the left side. It is possible that lead 56 would allow faster implant times in the operating room, because the physician could select which column of the first set of electrodes to use, or use both columns, at a later time. In addition, if the there are left to right asymmetries to the pain, then this lead could be placed on the physiological midline, and still give effects that are asymmetric to the right and left sides of the patient. In cases where activation of neurons is only desirable on one side of the body, the electrodes on the other side could be made anodal (+), thus preventing excitation on that side.

Figure 8:
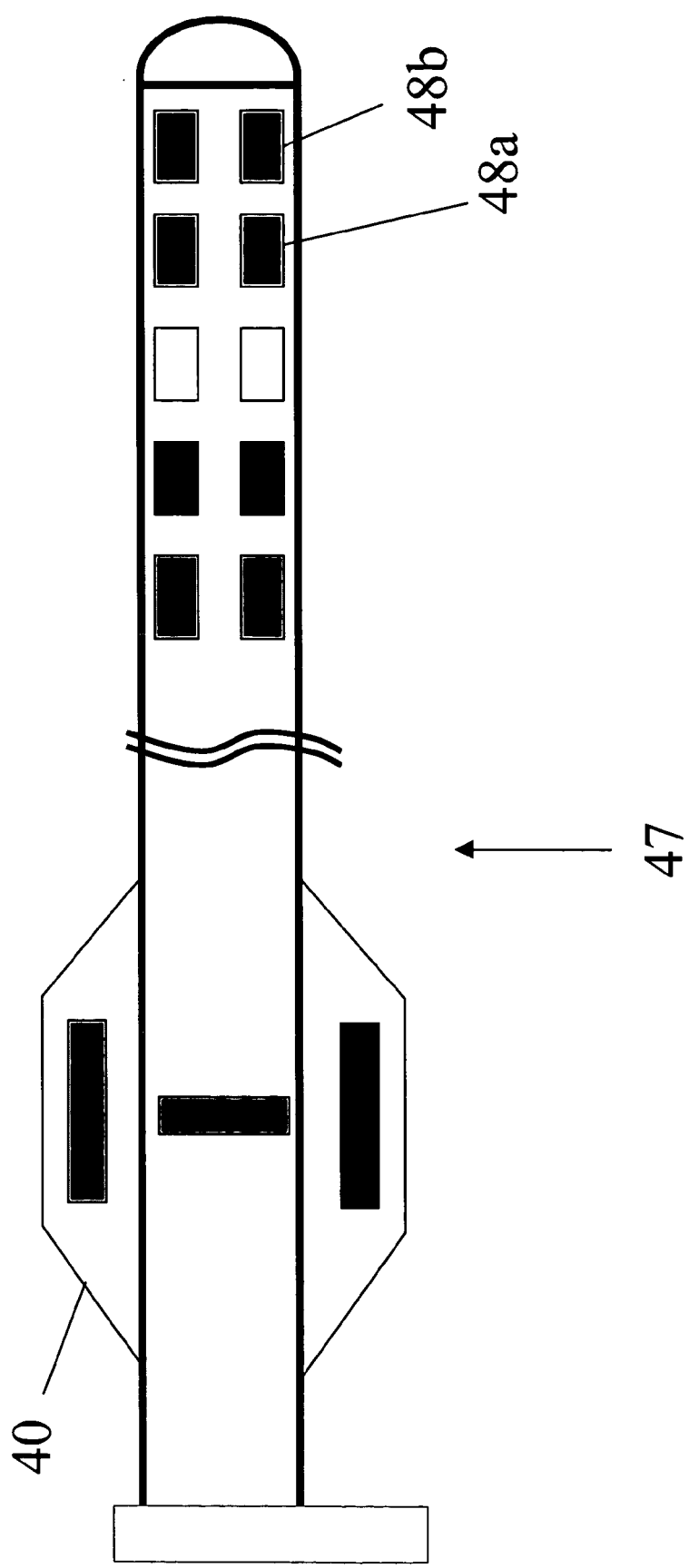
FIG. 8 is a ventral view of a lead that has a wider dimension along its entire length, that allows more stability of the LTS part to remain in contact with the dura.

FIG. 8 is ventral view of another embodiment of lead 23 specifically lead 47. The lead body of lead 47 has a wider dimension along its entire length. In one embodiment it may be paddle-like and about 4–5 mm in width. This might be easier to pass rostrally from the site of the laminectomy, which is required to insert the 10 mm or wider paddle portion 40. If the LTS part of the lead 47 is flat, it would give several advantages that paddle-type leads have. It could have electrodes only on the ventral surface, and insulation on the dorsal surface, thus preventing activation of neurons more dorsal than the dura. It also may have more lateral stability than a typical, cylindrical percutaneous type lead. As shown, there may be two columns of electrodes available for the LTS set, but one column may also be acceptable.

Figure 9:
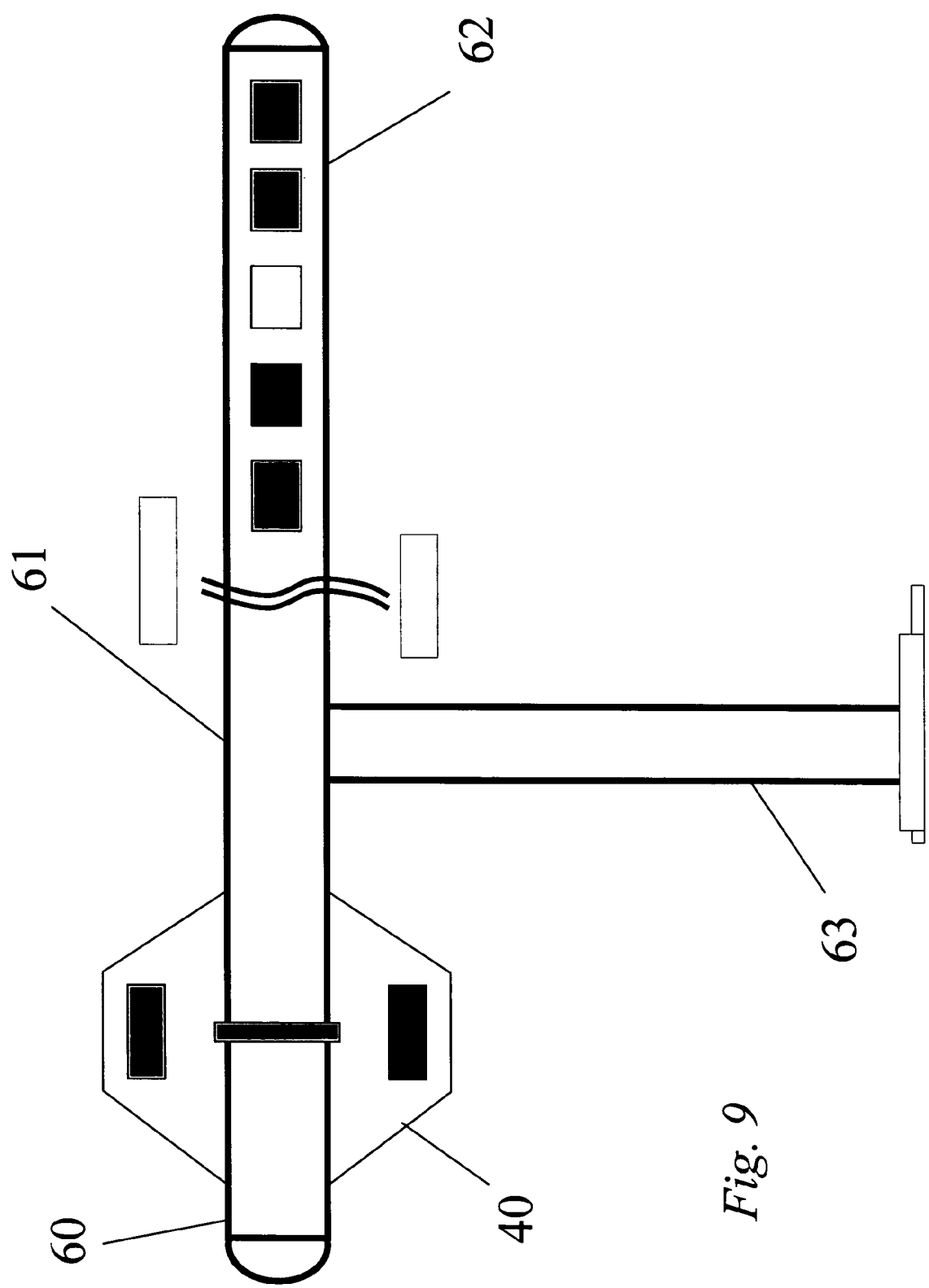
FIG. 9 is a ventral view of a lead that has a lead body that branches into two parts, with a TTS part that is inserted in a retrograde direction toward the patients' foot from the laminectomy site, and an LTS part that is inserted in an orthograde direction toward the patient's head from that same laminectomy site.

FIG. 9 is a ventral view of a lead that has a lead body 63 that branches into two parts, with a TTS part 60 that is inserted in a retrograde direction toward the patients' foot from the laminectomy site 61, and an LTS part 62 that is inserted in an orthograde direction toward the patient's head from that same laminectomy site. It is typical that paddle-type leads are inserted for one to three inches from a laminectomy site, so the TTS part 60 would be very near the branching point, but the LTS part 62 might be relatively longer, and can be easily passed from the laminectomy site to places more rostral.

Figure 10:
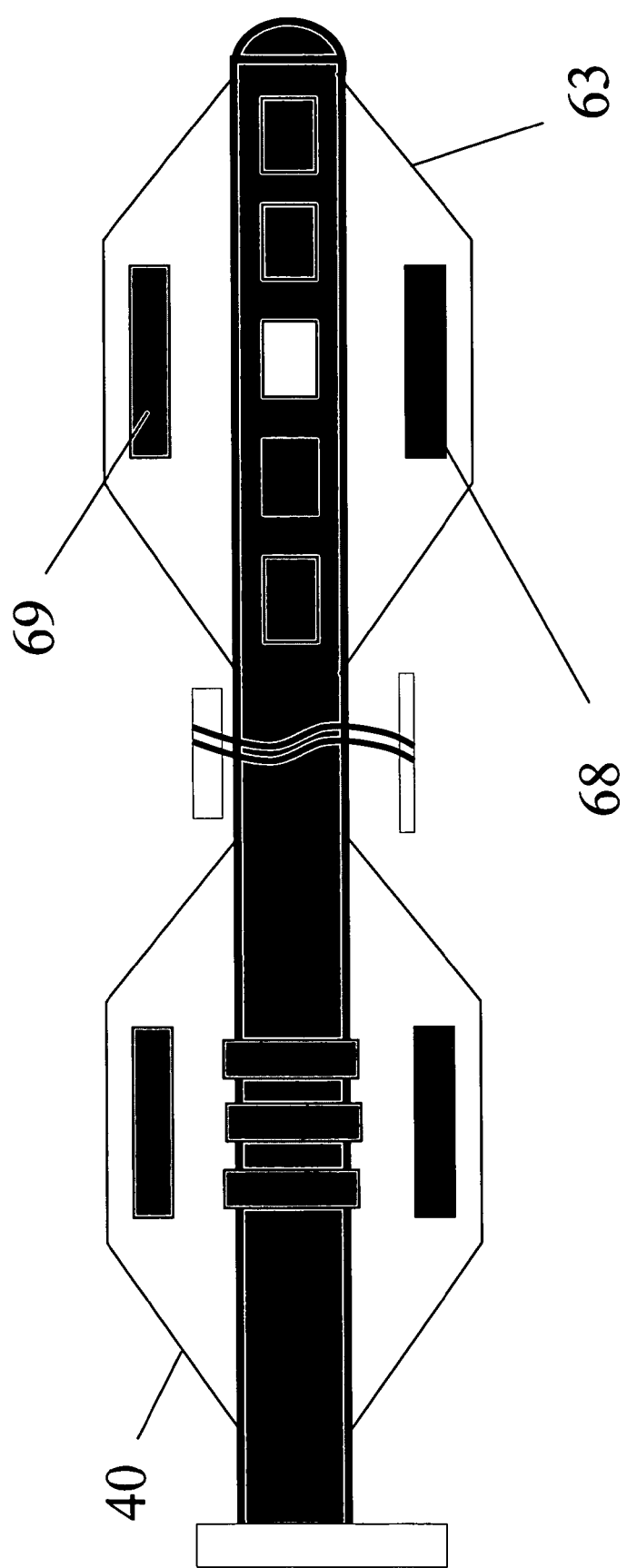
FIG. 10 is a ventral view of a lead which has two paddle parts, one with a TTS part and three possible central electrodes for control of leg and foot pain, and one with an LTS part, but also two more lateral, longitudinally-oriented electrodes that may be used to shield the roots with anodes.

FIG. 10 is a ventral view of the distal end of a lead which has two paddle parts, one with a TTS part 40 with three possible central electrodes for control of leg and foot pain, and one with an LTS part 63 which has not only five longitudinal electrodes, but also two more lateral, longitudinally-oriented electrodes 68 and 69 that may be used to shield the roots with anodes. This lead design allows the physician to program an LTS effect at T8–T10 to help back pain, but also, if activation of neurons on one side needs to be avoided, to make more lateral electrodes 68 or 69 anodes. The LTS part 63 may be on a paddle, which makes insertion from the laminectomy near the TTS part 40 difficult, or it may have thinner, insulative wings that wrap around the central cylindrical part and only deploy, with or without the aid of other instruments at the T8–T10 sites. Note that the lead may have the feature that the central electrodes on the TTS part are wider in dimension than their longitudinal extent, and the opposite it true of the LTS central electrodes.

Figure 11:
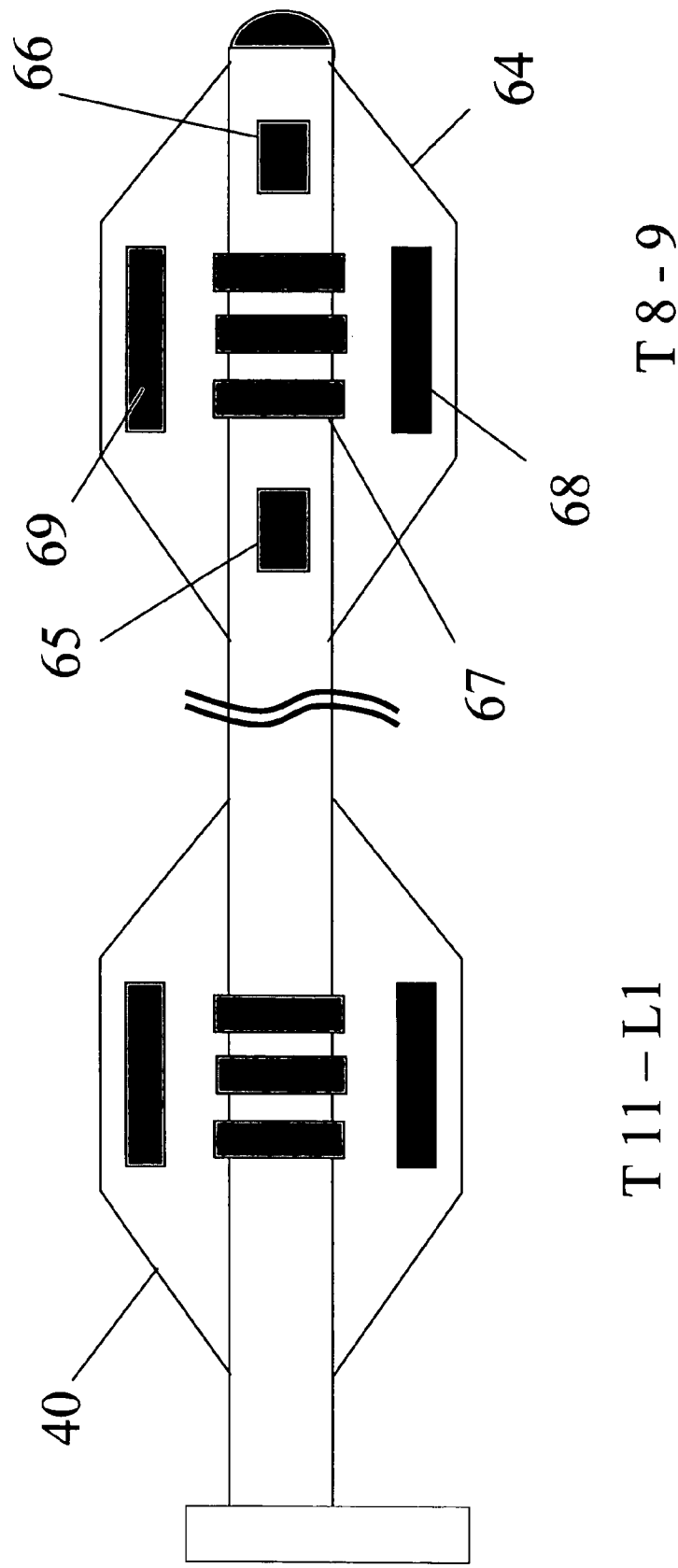
FIG. 11 is a ventral view of a lead that has two paddle parts, both of which have TTS abilities, but one can also use the LTS technique to optimally locate fields in a longitudinal direction.

FIG. 11 is a ventral view of a lead that has two paddle parts, both of which have TTS abilities. However, the more distal portion 64 can also use the LTS technique to optimally locate fields in a longitudinal direction because it has not only one or more electrodes 67 in the middle of the LTS set, but also extra electrodes in a longitudinal direction 65 and 66, for added programming ability to achieve LTS effects.

Figure 12:
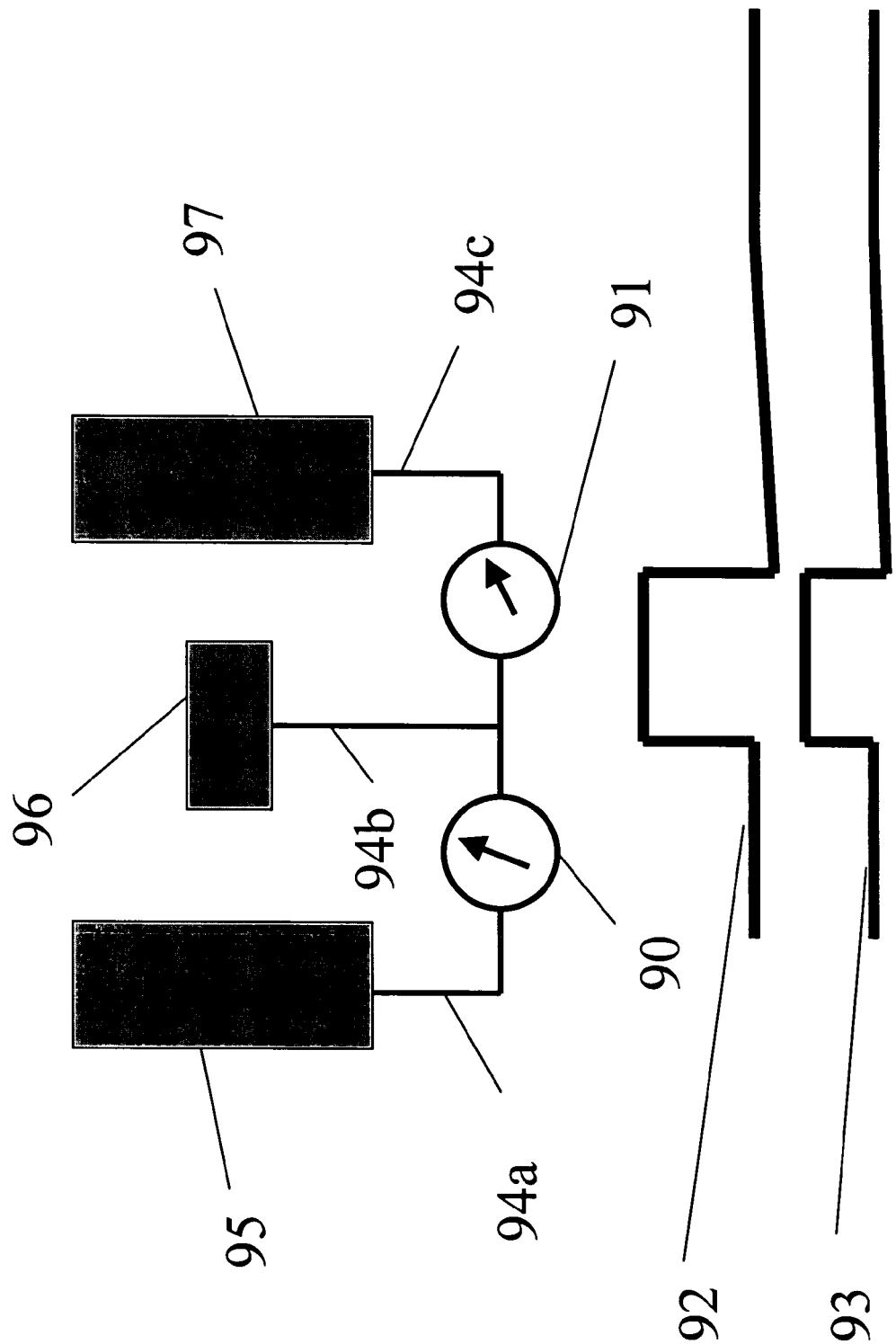
FIG. 12 is a schematic view of electrical pulse pairs generated by pulse generators, with their programmably different amplitudes that are delivered simultaneously among three electrodes in a tripole set, either LTS or TTS.

FIG. 12 is a schematic view of the concepts of the two patents that were cited above by Holsheimer J and Struijk J, U.S. Pat. No. 5,501,703 and U.S. Pat. No. 5,643,330. There are two electrical pulses 92 and 93, constituting a pulse pair, generated by the pulse generator which can produce voltage controlled or current controlled pulses 90 and 91, delivered by electrical wires 94a, 94b and 94c to three collinear electrodes 95, 96 and 97. At least one of the three electrodes will be the common ground for currents produced from the other two electrodes. The two pulses in a pair may have programmably different amplitudes and overlapping timings. In the current invention, two such pulses and electrode arrangements are utilized, one with LTS (longitudinal steered fields) and one with TTS (transversely steered fields) relative to the spinal cord.

Figure 13:
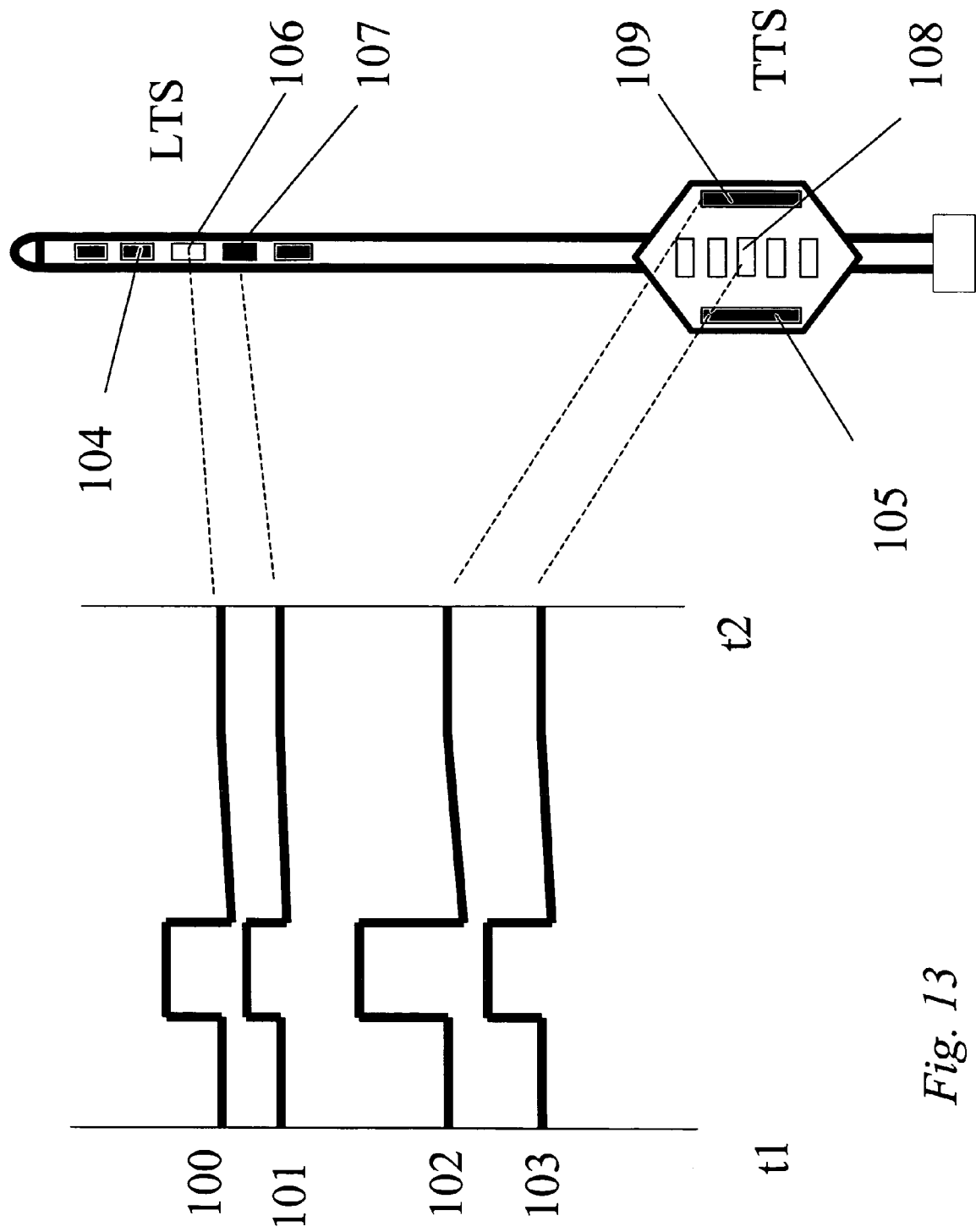
FIG. 13 is a schematic view of four approximately simultaneous in time pulses of programmably different amplitudes that are delivered to both two of three electrodes in an LTS set and to two of three electrodes in a TTS set, with at least one additional electrode in each set being a common ground.

FIG. 13 is a schematic view of four electrical pulses 100–103 that are substantially overlapping in time, with programmably different amplitudes, that have one pulse pair delivered to two of three electrodes in an LTS setting, e.g., 106 and 107, and one pulse pair to two of three electrodes in a TTS set, e.g., 108 and 109, with at least one additional electrode in each set being a common ground 104 and 105, respectively for those nearby active electrodes. In this case, the pulse generator can produce four simultaneous pulses of varying amplitudes, in the interval from t1 to t2, which is repeated, thus giving a pulse interval frequency of 1/(t2−t1). Pulse pairs 100 and 101 are delivered to the LTS set of electrodes at the distal portion of the lead, and can give relief of back pain. Pulse pairs 102 and 103 are delivered to the TTS set of electrodes at the paddle-like portion of the lead, and can give relief of leg and foot pain.

Figure 14:
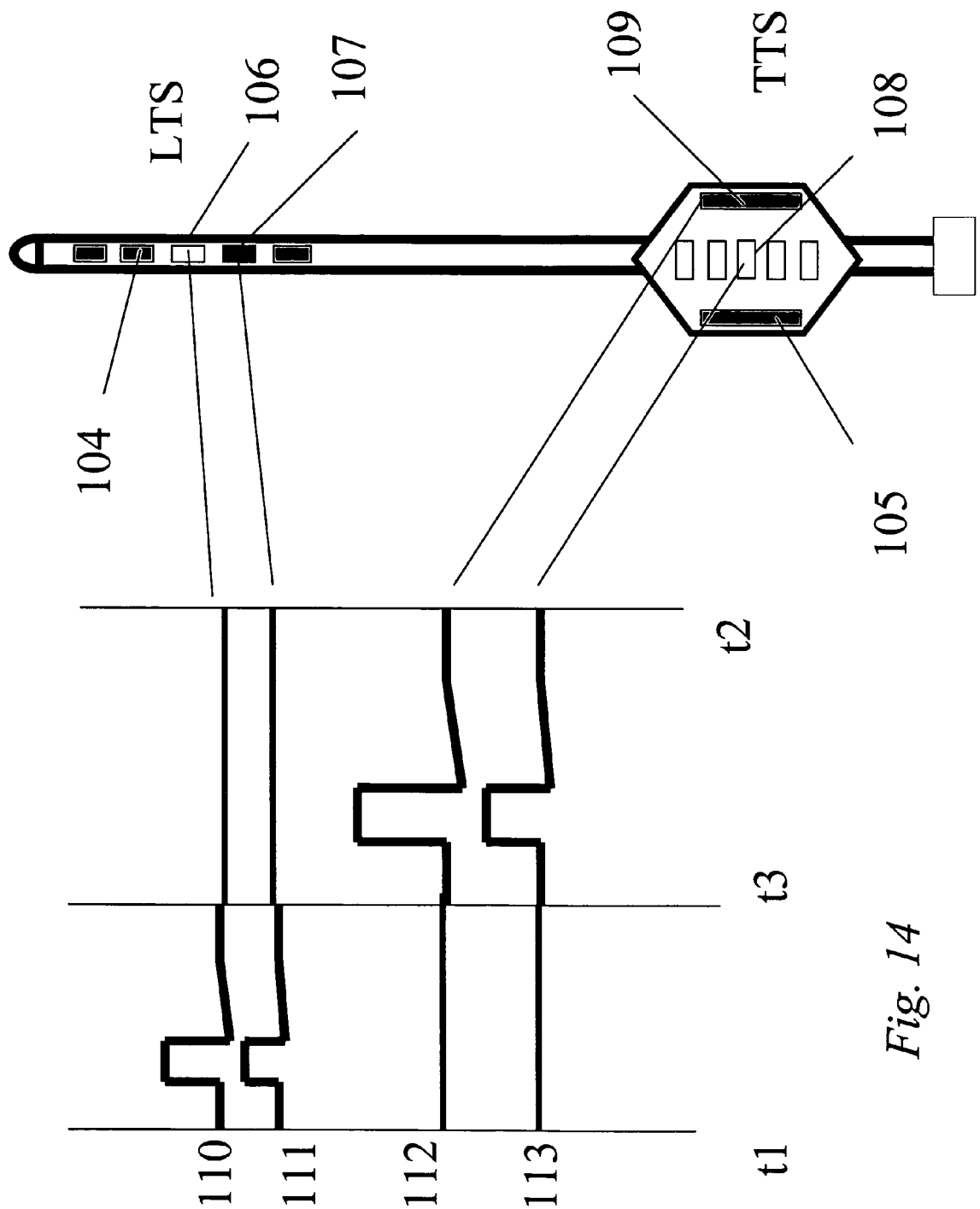
FIG. 14 is a schematic view of four pulses of programmably different amplitudes, that are delivered during two temporal phases, with the two pulse pairs of the first phase simultaneous and going to two electrodes in an LTS set, and the two pulse pairs of the second phase simultaneous and going to two electrodes in a TTS set, with at least one other electrode in each set being a common ground for pulses in that phase.

FIG. 14 is a schematic view of four pulses of programmably different amplitudes that are delivered during two temporal phases in an interval. This cycle is repeated, with an interval frequency of 1/(t2−t1). In this case, the pulse generator only needs to be able to produce two simultaneous pulses of different amplitude. During the first part of the interval, from t1 to t3, the two approximately overlapping pulses in pulse pair 110 and 111 are sent to electrodes in the LTS set, such as 106 and 107. One of the other electrodes 104 in the LTS set will be the common ground for the pulses 110 and 111. During the second part of the interval, from t3 to t2, two approximately overlapping pulses in pulse pairs 112 and 113 are sent to electrodes 108 and 109 in the TTS set, while electrode 105 is the common ground for the pulses 112 and 113. Again, the device can generate voltage controlled or current controlled pulses, and the common ground may be either anodal or cathodal.

Methods of stimulating two sites of neurological tissue are now described. One method involves implanting a lead in or near the spinal column. The lead has a first set of at least three electrodes, and a second set of at least first, second and third electrodes, wherein the first and second electrodes are positioned on opposite sides of an imaginary longitudinal axis that passes through the center of the third electrode. The lead is positioned with the first set of electrodes proximate a first section of the spinal column and with the second set of electrodes proximate a second section of the spinal column wherein the first section is at a higher vertebral level than the second section. In one embodiment, the first section is implanted at vertebral levels T6–T10 for treatment of low back pain. The second section may be implanted at vertebral levels T10–L1 for treatment of leg and foot pain. In one embodiment, the lead is implanted epidurally. At least one pulse generator is placed in electrical communication with the first and second sets of electrodes. The pulse generator then generates a first pulse and communicates the first pulse to the first set of electrodes. The pulse generator also generates a second pulse and communicates it to the second set of electrodes. In a preferred embodiment, the pulse generator provides two overlapping in time pulses to at least two of the electrodes in the second set of electrodes. In another preferred embodiment, the pulse generator may provide two overlapping in time pulses to at least two of the electrodes in the first set of electrodes. Furthermore, more than two overlapping in time pulses may be provided to the first or second sets of electrodes.

In one embodiment method, the lead is implanted in an orthograde direction. This may not require a laminectomy in cases where the lead is small enough for percutaneous insertion or folds or compresses in some way during insertion.

In one embodiment implantation technique relating to spinal cord stimulation, the physician may first perform a laminectomy at the site of placement of the second set of electrodes. The physician may then perform an orthograde insertion of the portion of the lead containing the first set of electrodes from the laminectomy site.

Some of the preferred dual sites for stimulation are identified in TABLE 1 below.

| Condition Treated by LTS (at least 3 electrodes approximately in a longitudinal column) | Site of LTS (longitudinal) electrodes | Condition Treated by TTS (second set of electrodes) | Site of TTS electrodes |
| --- | --- | --- | --- |
| Back pain | T6–T10 | Leg, foot, tailbone pain | T10–L1 |
| Back pain | T6–T10 | Sacral pain or pelvic organ pain | L1–S3 |
| Trunk, chest pain | T1–T8 | Leg, foot, tailbone pain | T10–L1 |
| Trunk, chest pain | T1–T8 | Sacral pain or pelvic organ pain | L1–S3 |
| Arm, shoulder, hand pain | C4–T1 | Leg, foot, tailbone pain | T10–L1 |

Examples of Field Steering with LTS

From 1997 to 2002, confidential clinical studies by Medtronic, Inc., were performed using screening devices (Screener Model 3669, Medtronic) on patients who were getting trial screening of SCS for chronic neuropathic pain. The patients were tested for several hours. They had percutaneously inserted SCS leads (PISCES®, Medtronic), each with four longitudinally arranged platinum-iridium electrodes, labeled E0 (top, rostral), E1, E2 and E3 (bottom, caudal). It is noted that concepts and effects of field steering for TTS (second set of electrodes) are set forth at Holsheimer J et al., U.S. Pat. No. 5,501,703, and Barreras et al., U.S. Pat. No. 5,895,416.

Figure 15:
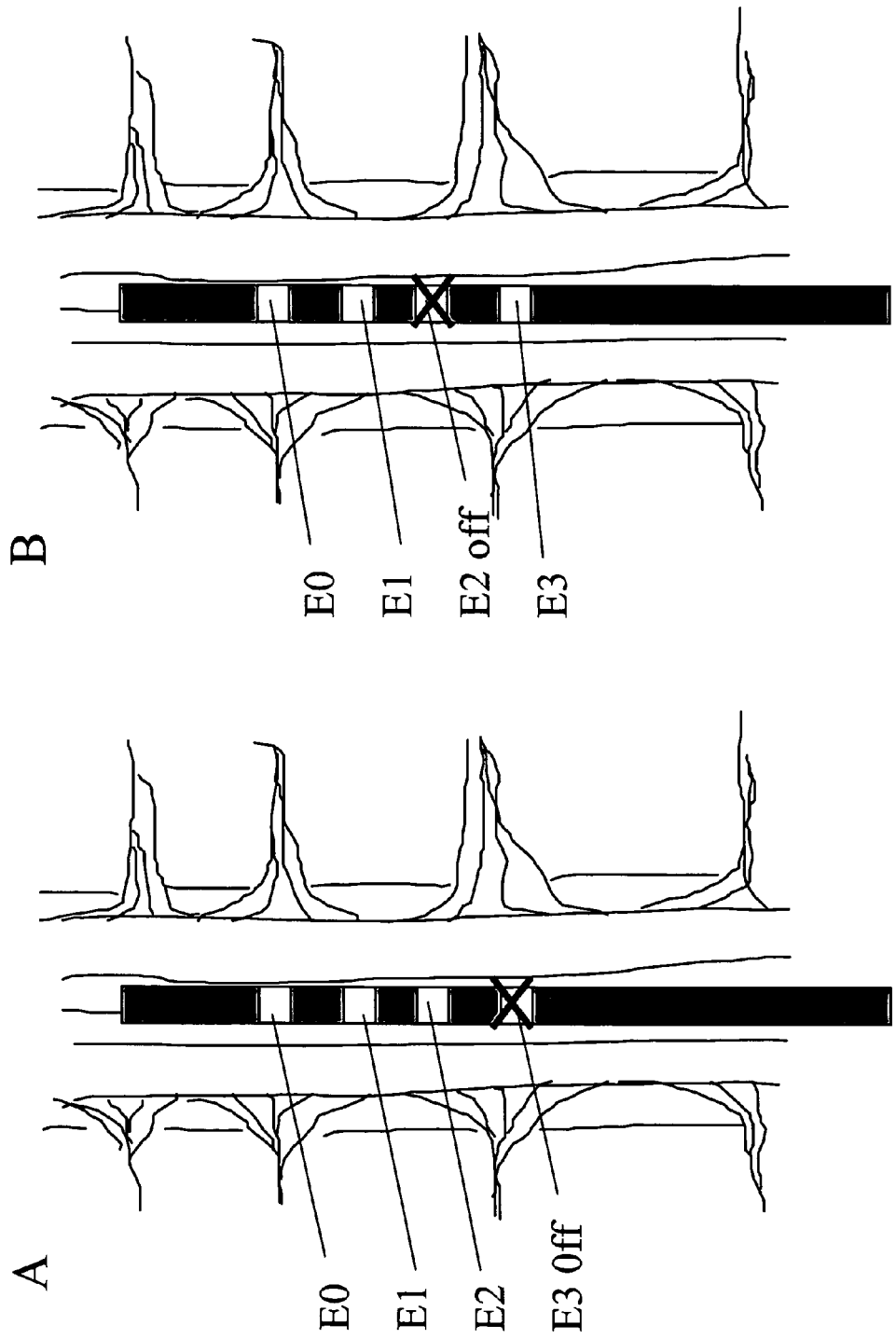
FIG. 15 depicts lead locations and electrode polarities of tight and stretched tripoles in two examples of patient data, for which there are maps of paresthesia.

FIG. 15 depicts lead locations and electrode polarities of tight 15A and stretched 15B tripoles in two examples of patient data, for which there are maps of paresthesia. The one electrode that is inactive in each case is marked by an "X". Three electrodes were always active. Electrode E1 always had the maximal cathodal pulse. In a regular "tight" tripole, the active electrodes were E0, E1, and E2, with E3 off (FIG. 15A). In a "stretched" tripole, the active electrodes were E0, E1 and E3, with E2 off (FIG. 15B). The screener could deliver a second simultaneous, voltage-controlled cathodal pulse to one of the outer active electrodes, while the other outer electrode was the anode, or common ground path. The fourth electrode on each lead was off. Thus, the simultaneous pulses in the pulse pair delivered to E1 and one outer electrode constituted LTS, since the electrodes are oriented parallel to the spinal cord axis, and there are two simultaneous pulses of varying amplitudes. Pulses were delivered at 50 Hz frequency, with a pulse width of 210 microseconds.

The pulse pairs sent to the electrodes had a "balance". With three active electrodes (two cathodes, one anode), balance, "B", could be any integer from +15 to −15. The center active electrode of the three was always a full cathode. When B=−15, the top, rostral electrode E0 was also a full cathode, with the same pulse as the middle active electrode. With each increase in B, the top electrode E0 had a cathodal pulse that was 6.67% less in amplitude. When B was zero, the top electrode E0 was a full anode, just like the bottom active electrode (E2 for a tight tripole, E3 for a stretched tripole). As B increased from +1 to +15, the bottom active electrode now had an increasingly negative, cathodal pulse. When B=+15, the bottom two active electrodes had full cathodal pulses, and the top electrode E0 was still an anode. Table 2 shows the relative amplitudes of the other electrodes when the electrode E1 has a pulse of −1.0 Volts.

TABLE 2. Relative voltages on the electrodes (E0=top/rostral, E3=bottom/caudal) when the cathodal pulse on electrode E1 is −1.0 Volt, with a longitudinal tripole stimulation (LTS) system, assuming the Pisces® lead was inserted in a rostral direction through a Tuohy needle. This table shows example settings for a voltage controlled pulse generator. It is importantly noted however that this invention includes current controlled or hybrid (combination of current controlled and voltage controlled) systems.

|  |  |  | Tight Tripole | | Stretched Tripole | |
| --- | --- | --- | --- | --- | --- | --- |
| Balance | E0 | E1 | E2 | E3 | E2 | E3 |
| B = 15 | 0 V | −1.0 V | −1.00 V | off | off | −1.00 V |
| B = 14 | 0 V | −1.0 V | −0.93 V | off | off | −0.93 V |
| B = 13 | 0 V | −1.0 V | −0.87 V | off | off | −0.87 V |
| B = 12 | 0 V | −1.0 V | −0.80 V | off | off | −0.80 V |
| B = 11 | 0 V | −1.0 V | −0.73 V | off | off | −0.73 V |
| B = 10 | 0 V | −1.0 V | −0.67 V | off | off | −0.67 V |
| B = 9 | 0 V | −1.0 V | −0.60 V | off | off | −0.60 V |
| B = 8 | 0 V | −1.0 V | −0.53 V | off | off | −0.53 V |
| B = 7 | 0 V | −1.0 V | −0.47 V | off | off | −0.47 V |
| B = 6 | 0 V | −1.0 V | −0.40 V | off | off | −0.40 V |
| B = 5 | 0 V | −1.0 V | −0.33 V | off | off | −0.33 V |
| B = 4 | 0 V | −1.0 V | −0.27 V | off | off | −0.27 V |
| B = 3 | 0 V | −1.0 V | −0.20 V | off | off | −0.20 V |
| B = 2 | 0 V | −1.0 V | −0.13 V | off | off | −0.13 V |
| B = 1 | 0 V | −1.0 V | −0.07 V | off | off | −0.07 V |
| B = 0 | 0 V | −1.0 V | 0 V | off | off | 0 V |
| B = −1 | −0.07 V | −1.0 V | 0 V | off | off | 0 V |
| B = −2 | −0.13 V | −1.0 V | 0 V | off | off | 0 V |
| B = −3 | −0.20 V | −1.0 V | 0 V | off | off | 0 V |
| B = −4 | −0.27 V | −1.0 V | 0 V | off | off | 0 V |
| B = −5 | −0.33 V | −1.0 V | 0 V | off | off | 0 V |
| B = −6 | −0.40 V | −1.0 V | 0 V | off | off | 0 V |
| B = −7 | −0.47 V | −1.0 V | 0 V | off | off | 0 V |
| B = −8 | −0.53 V | −1.0 V | 0 V | off | off | 0 V |
| B = −9 | −0.60 V | −1.0 V | 0 V | off | off | 0 V |
| B = −10 | −0.67 V | −1.0 V | 0 V | off | off | 0 V |
| B = −11 | −0.73 V | −1.0 V | 0 V | off | off | 0 V |
| B = −12 | −0.80 V | −1.0 V | 0 V | off | off | 0 V |
| B = −13 | −0.87 V | −1.0 V | 0 V | off | off | 0 V |
| B = −14 | −0.93 V | −1.0 V | 0 V | off | off | 0 V |
| B = −15 | −1.00 V | −1.0 V | 0 V | off | off | 0 V |

Figure 16:
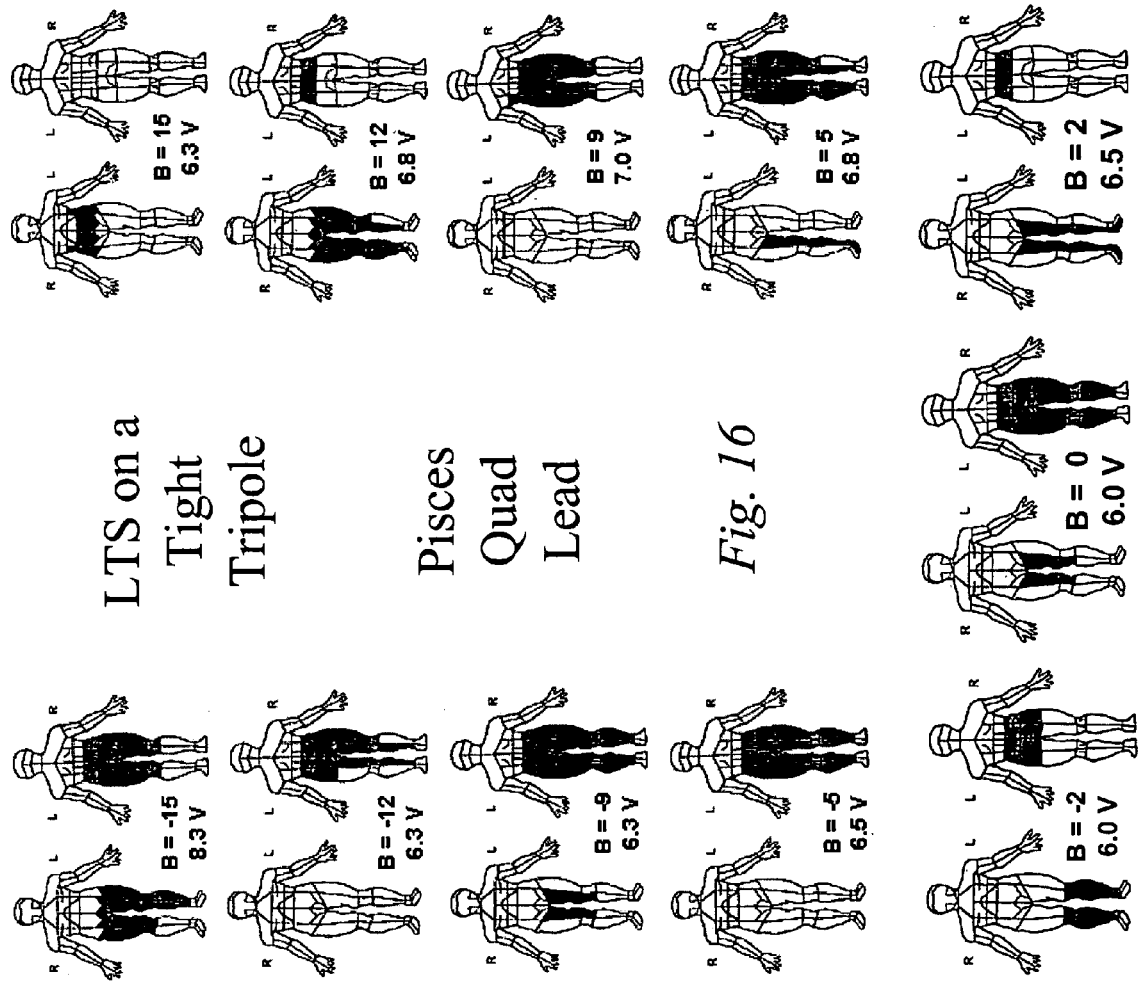
FIG. 16 depicts locations of paresthesia on body maps of a patient with a single percutaneous 4 electrode lead at vertebral level T9 which uses the LTS technique to control and steer the electric fields, using three neighboring electrodes, a tight tripole.

FIG. 16 depicts locations of paresthesia on body maps of a patient with a single percutaneous PISCES® four electrode lead at the junction of vertebral levels T9 and T10 which uses the LTS technique to control and steer the electric fields, using three neighboring active electrodes, E0, E1 and E2, a tight tripole. Each inset figure has the balance, B, and the voltage amplitude of the electrode E1 pulse at which the paresthesia was drawn. These voltages were the highest that the patient could tolerate. Optimal paresthesia for low back pain would have zones in the back shaded, but not those of the abdomen or groin, which are uncomfortable or cause cramping. Paresthesia shown by shading of zones in the legs is less desirable, but not something that is prohibitive for long term SCS usage. Note that of the three balances that a conventional, full-polarity SCS device could produce (B=0, +15 or −15), only one with B=0 would avoid paresthesia in the abdomen or groin.

Figure 17:
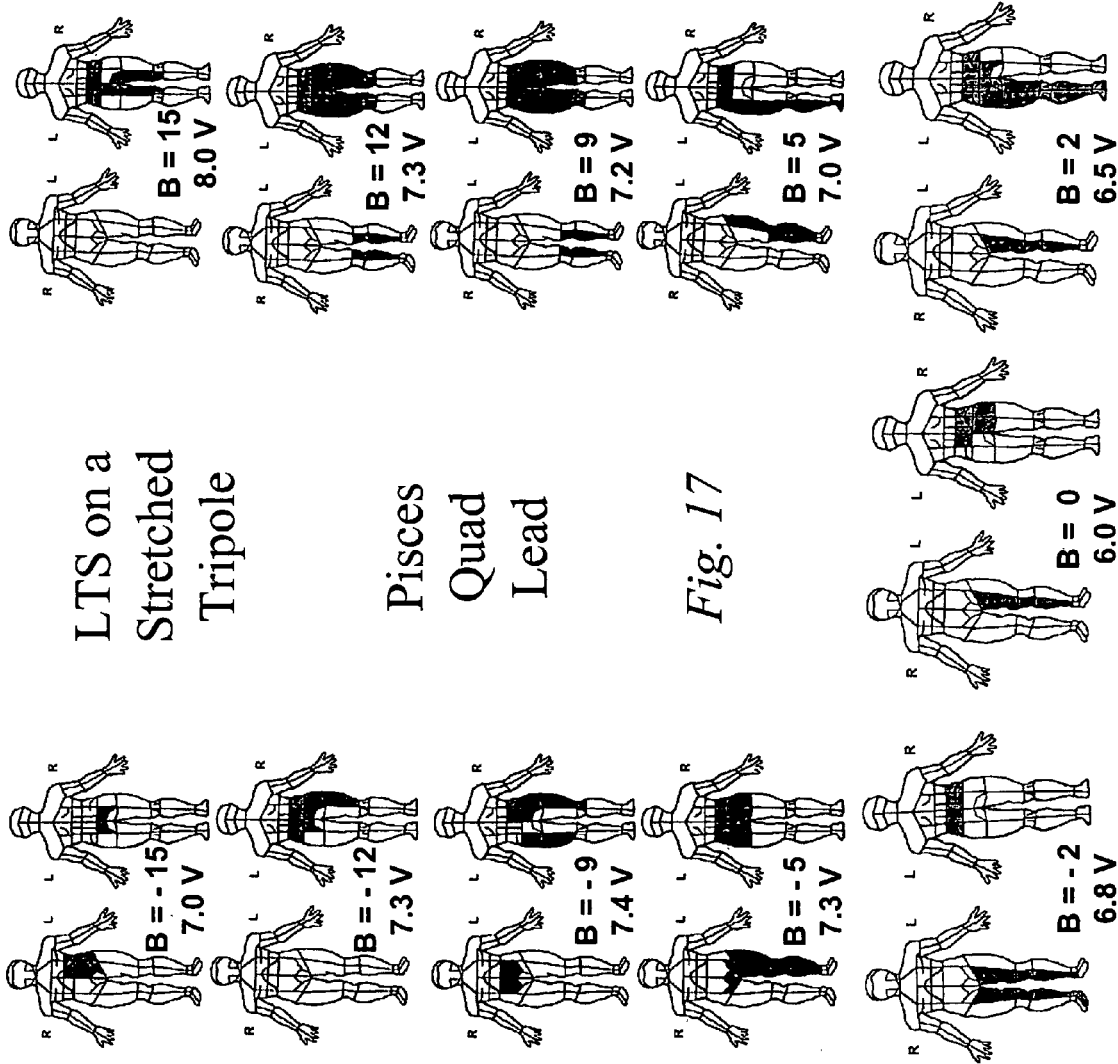
FIG. 17 depicts locations of paresthesia on body maps of a patient with a single percutaneous four electrode lead at vertebral level T9 which uses the LTS technique to control and steer the electric fields, using three active electrodes and one inactive electrode in the middle, a stretched tripole.

FIG. 17 depicts locations of paresthesia on body maps of a patient with a single percutaneous PISCES® four electrode lead at vertebral level T9 which uses the LTS technique to control and steer the electric fields, using three electrodes and one electrode inactive in the middle, i.e., a stretched tripole. Several balances that gave paresthesia into the abdomen or groin, which would be unacceptable over long times, are B=−15, −9, and −5. Note that several balances gave paresthesia on most of the back, including B=−12, but that it might be experienced on one side more than the other. Some balances have no paresthesia on the front of the legs, such as B=−12 and B=+15.

There are subtle but important differences in paresthesia, depending upon balance. Shifting of balance by a small amount, by balances of two or three steps, can mean the difference between abdominal or groin paresthesia, or not. When some patterns give no paresthesia on the front of the legs, or parts of the back of the legs, these may be preferred, in order to keep the strongest paresthesia in the buttocks and back. Few maps indicate paresthesia in the small of the back, above the beltline, and this was due to the location of the lead being at the bottom of T9. Percutaneous leads that have electrodes higher than this can give higher paresthesia.

In addition, the pulses delivered could be voltage controlled, current controlled, or a hybrid combination of the two. The balance of pulse pairs need not be discrete, like the 31 steps tested so far. The amplitudes could be independently varied to a fine degree, so effectively the differences in the amplitudes would be determined nearly in an analog fashion. Paddle-type leads could be used instead of percutaneously inserted cylindrical leads. Leads could be place below the dura. The pulse pairs could be anodal, with a cathode being the common ground.

Thus, embodiments of the Stimulation Apparatus and Method to Treat Multiple Sites are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device comprising:
  (a) a pulse generator capable of generating stimulation pulses, wherein the stimulation pulses have a pulse amplitude; and
  (b) an implantable lead having a proximal portion and a distal portion, the lead comprising:
    (i) a lead body;

(ii) a first set of electrodes coupled to the lead body, the first set of electrodes including at least three electrodes in electrical communication with the pulse generator; and (iii) a second set of electrodes coupled to the lead body, the second set of electrodes including at least first, second and third electrodes in electrical communication with the pulse generator, wherein the first and second electrodes are positioned on opposite sides of an imaginary longitudinal axis of the lead body that passes through the center of the third electrode, and wherein the second set of electrodes are located at or nearer to the proximal portion of the lead relative to the location of the first set of electrodes; and wherein a first distance between the distal most electrode of the second set of electrodes and the proximal most electrode of the first set of electrodes is at least three centimeters.

2. The implantable medical device of claim 1 wherein the pulse generator is capable of independently controlling the pulse amplitude on all three electrodes of the second set of electrodes.

3. The implantable medical device of claim 2 wherein the pulse generator is capable of independently controlling the pulse amplitude on all three electrodes of the first set of electrodes.

4. The implantable medical device of claim 1 wherein the first distance is at least four centimeters.

5. The implantable medical device of claim 1 wherein the first distance is at least five centimeters.

6. The implantable medical device of claim 1 wherein the first distance is at least six centimeters.

7. The implantable medical device of claim 1, wherein the lead body has a first width at the first set of electrodes and a second width at the second set of electrodes, wherein the first width is smaller than the second width.

8. The implantable medical device of claim 7 wherein the first width is no greater than 0.8 times the second width.

9. The implantable medical device of claim 7 wherein the first width is no greater than 0.7 times the second width.

10. The implantable medical device of claim 7 wherein the first width is no greater than 0.6 times the second width.

11. The implantable medical device of claim 7 wherein the first width is no greater than 0.5 times the second width.

12. An implantable lead having a proximal portion and a distal portion, the lead comprising:

(a) a lead body;

(a) a first set of electrodes coupled to the lead body, the first set of electrodes including at least three electrodes configured to receive pulses from at least one pulse generator; and (b) a second set of electrodes coupled to the lead body, the second set of electrodes including at least first, second and third electrodes configured to receive pulses from the at least one pulse generator, wherein the first and second electrodes are positioned on opposite sides of an imaginary longitudinal axis of the lead body and that passes through the center of the third electrode, and wherein the second set of electrodes are located at or nearer to the proximal portion of the lead relative to the location of the first set of electrodes, and wherein a first distance between the distal most electrode of the second set of electrodes and the proximal most electrode of the first set of electrodes is at least three centimeters.

13. The implantable lead of claim 12, further comprising a first electrical conductor coupled to the first electrode, a second electrical conductor coupled to the second electrode, and a third electrical conductor coupled to the third electrode, wherein each of the first, second and third electrical conductors are capable of providing electrical pulses to the first, second and third electrodes respectively when coupled to a pulse generator.

14. The implantable lead of claim 12 wherein the first distance is at least four centimeters.

15. The implantable lead of claim 12 wherein the first distance is at least five centimeters.

16. The implantable lead of claim 12 wherein the first distance is at least six centimeters.

17. The implantable lead of claim 12, wherein the lead body has a first width at the first set of electrodes and a second width at the second set of electrodes, wherein the first width is smaller than the second width.

18. The implantable lead of claim 17 wherein the first width is no larger than 0.7 times the second width.

19. The implantable lead of claim 17 wherein the first width is no greater than 0.5 times the second width.

20. The implantable lead of claim 12 wherein the first, second and third electrodes are collinear and a line passing through the centers of the first, second and third electrodes is perpendicular to the imaginary longitudinal axis.

* * * * *